United States Patent [19]

Odensten et al.

[11] Patent Number: 4,823,780
[45] Date of Patent: Apr. 25, 1989

[54] DRILL GUIDING AND ALIGNING DEVICE

[76] Inventors: Magnus G. Odensten, Hjulsbrovägen 104, S-582 69 Linköping; Jan I. Gillquist, Stjärnorpsvägen Berg, S-590 61 Vreta Kloster, both of Sweden

[21] Appl. No.: 803,401
[22] PCT Filed: Mar. 13, 1985
[86] PCT No.: PCT/SE85/00114
§ 371 Date: Nov. 5, 1985
§ 102(e) Date: Nov. 5, 1985
[87] PCT Pub. No.: WO85/04092
PCT Pub. Date: Sep. 26, 1985

[30] Foreign Application Priority Data

Mar. 14, 1984 [SE] Sweden ............................ 8401427

[51] Int. Cl.⁴ ............................................. A61F 5/04
[52] U.S. Cl. ............................. 128/92 VD; 623/13; 408/72 B
[58] Field of Search ....... 128/92 VD, 92 VZ, 92 YK, 128/92 YV, 92 YF, 92 YE, 92 V, 92 VY, 92 VV, 92 VW, 83; 408/72 B, 72 R, 97, 115 B, 115 R; 623/13, 18, 19, 20, 39

[56] References Cited

U.S. PATENT DOCUMENTS

| | | |
|---|---|---|
| 3,097,891 | 7/1963 | Brideau .......................... 408/72 B X |
| 3,363,488 | 1/1968 | Thau et al. ........................... 408/97 |
| 3,704,707 | 12/1972 | Halloran ......................... 128/92 VD |
| 4,037,592 | 7/1977 | Kronner ........................... 128/92 VD |
| 4,235,428 | 11/1980 | Davis ........................ 128/92 VD X |
| 4,257,411 | 3/1981 | Cho .................................. 128/92 VD |
| 4,444,180 | 4/1984 | Schneider et al. ............ 128/92 VD |
| 4,535,768 | 8/1985 | Hourahane et al. ...... 128/92 VD X |
| 4,590,928 | 4/1986 | Hunt et al. ........................ 623/13 X |
| 4,622,959 | 11/1986 | Marcus ........................... 128/92 VD |

FOREIGN PATENT DOCUMENTS

| | | |
|---|---|---|
| 0126520 | 2/1984 | European Pat. Off. .............. 623/13 |
| 2747568 | 4/1979 | Fed. Rep. of Germany ........ 623/13 |

OTHER PUBLICATIONS

Drill Guides for Improving Accuracy in Anterior Cruciate Ligament Repair and Reconstruction—George F. Hewson, Jr., MD.

Primary Examiner—Richard J. Apley
Assistant Examiner—David J. Bender
Attorney, Agent, or Firm—Banner, Birch, McKie & Beckett

[57] ABSTRACT

In a device for aligning and guiding a reciprocatingly movable drill rod (11) for drilling a hole (A', B') through at least either the tibia (B) or the femur (A) forming the knee joint, the hole being intended to receive one end of an anterior cruicate ligament, which is then attached to the bone. The device includes a first tube-like aligning and guiding element (5) which is intended to be introduced into and aligned in the space between the condyles of the femur (A) over the plateau of the tibia (B) and the ends of which are spaced apart at a distance corresponding to the length of the cruciate ligament, and a second aligning and guiding element (9) which is in line with the first element and located externally of the aforementioned space, and which is located from the first element at a distance which is at least partially bridged by a part of the tibia or femur located adjacent the space.

2 Claims, 2 Drawing Sheets

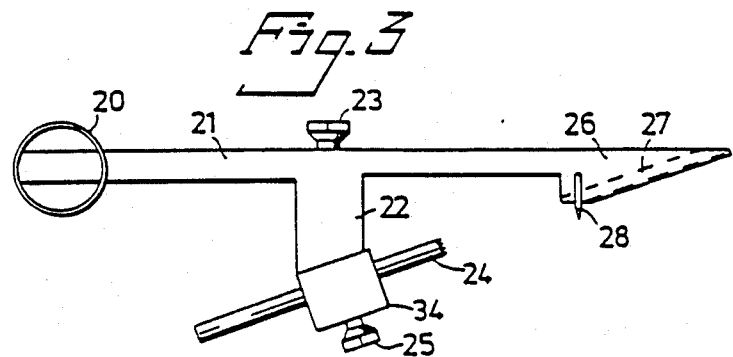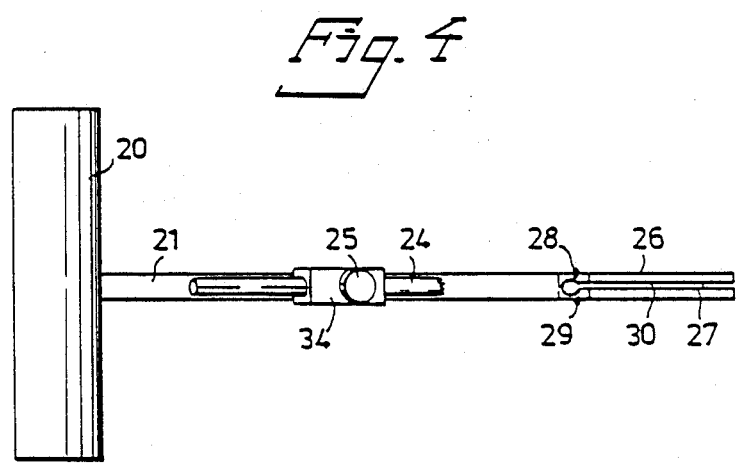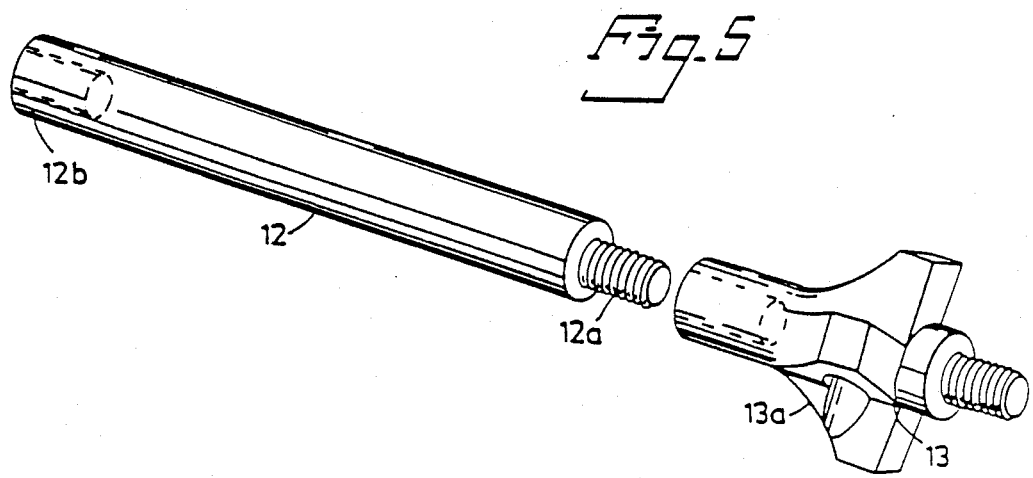

DRILL GUIDING AND ALIGNING DEVICE

TECHNICAL FIELD

The present invention relates to a device for aligning and guiding a reciprocatingly moveable drill rod to facilitate drilling a hole through at least either the tibia or the femur part of a knee joint, the hole being intended to receive one end of an anterior cruciate ligament substitute, which is then fastened to the bone. The invention also relates to a drill rod and a milling device to be used in connection with the device.

BACKGROUND ART

When carrying out a surgical operation in which an anterior cruciate ligament substitute is to be inserted in the tibia and the femur it is essential that the ends of the cruciate ligament are fastened so that the attachment locations are isometrically positioned, i.e. so that the distance between these locations, and therewith the length of the substitute ligament, will not change during angular movement of the tibia relative to the femur through 0° to about 140°.

Many methods have been proposed for determining firstly the precise positions of these attachment locations and secondly the alignment of the holes, canals and the like formed in the bone and serving as guide and/or attachment means for the cruciate ligament. Various instruments and devices for facilitating the alignment and guidance of tools for drilling the aforesaid holes or for forming said canals etc have also been proposed.

A number of these known methods and devices are described and illustrated in U.S. Pat. No. 4,257,411 and in the article "Drill Guides for Improving Accuracy in Anterior Cruciate Ligament Repair and Reconstruction" written by George F Hewson Jr. and published in the journal "Clinical Orthopaedics and Related Research", No. 172, Jan.-Feb. 1983.

The aforementioned known methods and devices are encumbered with a number of disadvantages, however. For example, even though it has been possible to determine the positions of the attachment points with relative precision, it has not been possible to drill holes so that the mouths thereof facing said attachment points coincide with the attachment points, since the holes must be drilled from outside the tibia or the femur respectively. In addition hereto, the holes are drilled in two different working stages, often with the use of two different drill aligning and guiding devices. Moreover, it has not been possible to make the edges of such mouths smooth due to the inaccessibility of the space between the bones.

DISCLOSURE OF THE INVENTION

It is an object of the present invention to improve previously known devices and to provide a drill aligning and guiding tool with which the holes intended for attachment of the cruciate ligament substitute can be drilled precisely at desired locations in the tibia and femur, and also in one and the same working operation. It is also an object of the invention to provide a drill aligning and guiding tool capable of lateral removal from the drill rod.

BRIEF DESCRIPTION OF THE DRAWINGS

FIG. 3 is a side view of a modification of the device shown in FIG. 1, FIG. 4 is a top view seen from below in FIG. 3, FIG. 5 is a perspective view of a first embodiment of a device for milling the outer edges of the holes passing through the tibia and femur.

PREFERRED EMBODIMENTS

Figure 1:
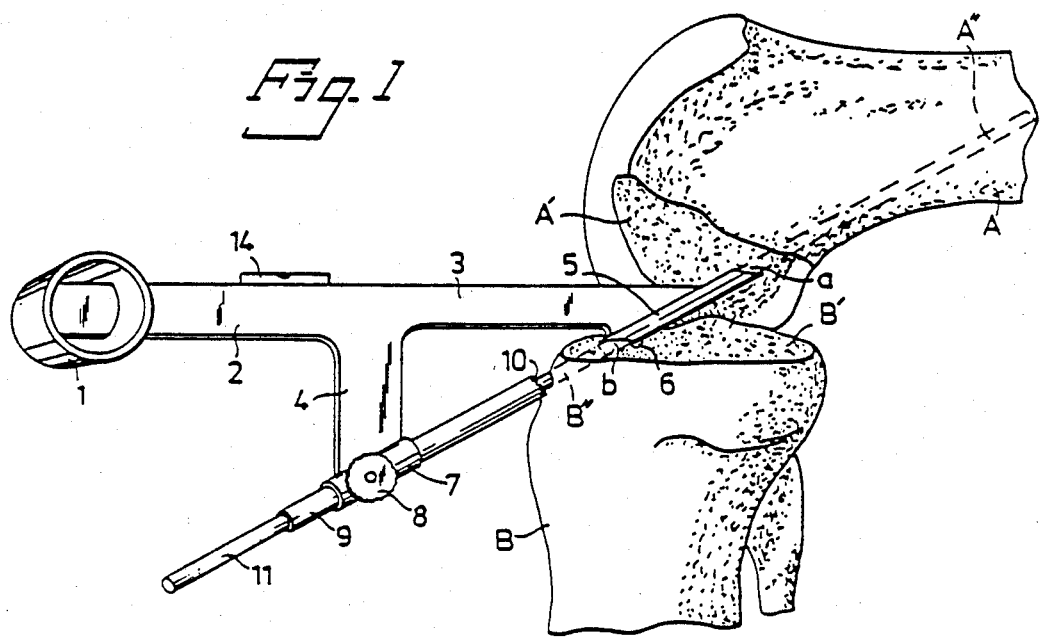
FIG. 1 is a schematic perspective side view of parts of a knee joint and of a device according to the invention.

FIG. 1 illustrates those parts of the knee joint of a right leg which includes a femur A exhibiting the two femoral condyles of which the nearest (inner) is cut away and the distal (outer) is referenced A', and a tibia B exhibiting a plateau surface B' at its upper end The centre for attachment of an anterior cruciate ligament (not shown) to the inner surface of the femoral condyle A' is referenced a, while the centre for attachment of the cruciate ligament to the plateau B' is referenced b.

Before implanting an anterior cruciate ligament substitute into the knee there is made in the anterior part thereof an opening via which an instrument can be inserted into the space between the tibia and femur in order to enlarge the space between the condyles by, inter alia, removing the residual parts of the end of the damaged anterior cruciate ligament attached to the femur. The centre b is then determined, either by localizing visually the attachment point of a residual part of the end of the damaged cruciate ligament in the tibia, or by measurement in those cases where it is impossible to determine the point at which the damaged ligament is attached to the tibia.

Anatomical studies have shown that the angle subtended by the anterior cruciate ligament and the longitudinal axis of the femur is approximately 28° and that the centre a for the attachment point of the anterior cruciate ligament of the femur A is located at a distance of approximately 31 mm from the centre b of the attachment point of the anterior cruciate ligament to the tibia B when the longitudinal axes of the femur and tibia form a right angle with one another. It follows from this that the normal length of the cruciate ligament at this angle is approximately 31 mm. Because of the isometric positioning of the centres a and b this length will remain unchanged, even when the angle is changed to values within the range 0°-approx. 140°.

The device according to the invention has been designed on the basis of the findings of these studies.

The device comprises a tubular handgrip 1 attached to a handle 2 having two arms 3 and 4. Mounted on the distal end of the arm 3 so as to form an angle of 28° with the handle 2 is a tube 5. The two ends of the tube 5 are bevelled so as to be parallel with the handle 2 and are spaced 31 mm apart. The end of the tube 5 facing the arm 4 is provided with a pointed projection 6. Attached to the end of the arm 4 remote from the handle 2 is an outer sleeve or tube 7 provided with a screw 8 An inner sleeve or tube 9 having an outer diameter which is negligibly smaller than the inner diameter of the outer tube 7 is mounted for axial movement in the outer tube and can be locked in selected axial positions relative thereto by means of the screw 8. The longitudinal axes of the tubes 7 and 9 are located in line with the longitudinal axis of the tube 5 and, similar to the longitudinal axis of said tube 5, form an angle of 28° with the handle 2.

Subsequent to swinging the femur to an angle of 90° to the tibia, as illustrated in FIG. 1, and determining the location of the centre b, the tube 5 of the device is inserted through the opening formed in the anterior part of the knee. In FIG. 1 the handle 2 is held horizontally and the end of the tube 5 facing the tubes 7 and 9 is located immediately above the centre b, whereafter the point 6 is pressed into the plateau B' of the tibia. The device is then swung about the longitudinal axis of the handle 2 and/or in the horizontal plane around the point 6 until the end of the tube 5 remote from the tubes 7 and 9 abuts the inner surface of the condyle A'. Because of the afore-described dimensioning of the device and its alignment relative to the leg parts A and B located at right angles to one another, this lastmentioned end of the tube 5 will be located in the middle of the centre a, i.e. exactly at the location of the attachment of the anterior cruciate ligament to the femur.

With the device in this last mentioned position of alignment, the tube 9 is urged against the tibia B until a sawtooth edge 10 on said tube enters the tibia in the manner shown in FIG. 1, whereafter the screw 8 is tightened. The device is therewith held in its set position and drilling can commence.

A drill rod 11 fitted to a drilling machine, not shown, is inserted into the tube 9 until the free end of the drill rod abuts the tibia. The drilling machine is then started and the rotating drill pressed against the tibia until a hole B'' is drilled therethrough. The drill is then displaced further in through the tube 5 and pressed against the femoral condyle A' until a hole A'' has been drilled therethrough. The drill is then withdrawn from the tube 5 and the tube 9 and the screw 8 is slackened off, whereafter the device is removed from the knee.

A modification of the device in FIG. 1 is shown in FIGS. 3 and 4. The device in FIGS. 3 and 4 essentially corresponds to, and is used in, the same manner as the device according to FIG. 1. Therefore, only details of the device of FIGS. 3 and 4 not found in, or modified with respect to FIG. 1 will be described below.

The modified device consists of a handgrip 20, a handle 21, an arm 22, a holder 34 detachably connected to the arm 22 by means of a screw 23, a passage (not shown) in the holder, said passage having a circular cross section, a tube 24 reciprocally and detachably mounted in said passage with the aid of a screw 25, and a front end portion 26 containing a tube or a passage 27 having a circular cross section and aligned with tube 24. On each side of the mouth of the passage 27 facing the tube 24 is mounted a pin 28 and 29, respectively. A slot 30 is formed in the end portion 26 in such a manner that the passage 27 will be open downwardly in FIG. 3 along the whole length thereof. The width of the slot 30 is substantially less than the diameter of the passage 27.

Figure 2:
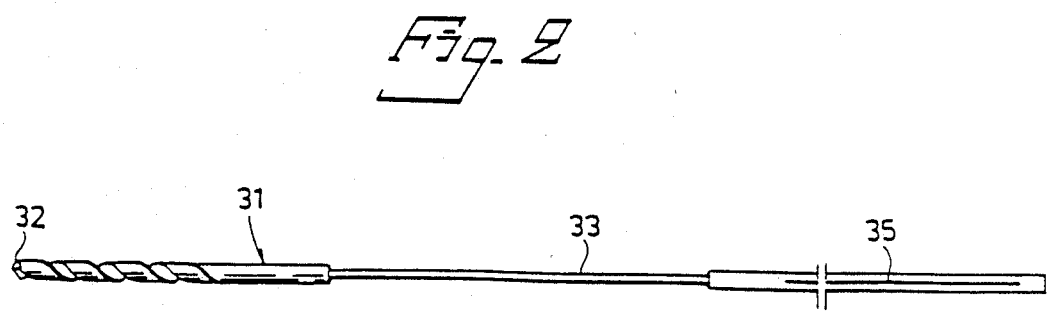
FIG. 2 is a side view of a drill rod according to the invention.

The drill rod according to the invention is shown in FIG. 2 and is designated 31. It is formed as a twist drill having cutting edges along substantially its whole length or only at its tip 32. The diameter of the drill rod 31 is somewhat less than the inner diameters of the passage 27 and tube 24 and the rod is substantially longer than the distance between the mutually remote ends of the end portion 26 and the tube 24. The drill rod has an approximately central flat portion 33. The diameter of the drill rod may be approximately 3 mm and its length approximately 240 mm. The flat portion may have a thickness of approximately 1.7 mm and a length of approximately 60 mm which is longer than the length of the passage 27. After drilling holes in the two bones as shown in, and described above in connection with FIG. 1, by means of the drill rod 31 and the device shown in FIGS. 3 and 4, the holder 34 and thus the tube 22 is loosened from the arm 22 by unscrewing the screw 23, whereupon the holder and the tube are pulled off the drill rod after the drilling machine has been disconnected from the drill rod. The drill rod 31 is then rotated about its longitudinal axis until one of two scribed lines 35, one on each side of the rod, and visible on the portion of the rod situated outside the tibia, has been set in line with the slot 30 to the passage 27. This results in that the flat portion 33, which is partly within the passage is set so that its smallest dimension will be in alignment with the width of the slot 30. The device may now be removed from the drill rod via the slit 30 by displacing the device generally perpendicularly away from the drill rod.

The reason why the drill rod 31 shall maintain its position in the holes of the tibia and of the femur while and after the device is removed is that the drill rod shall act as a guide for a drill tube. This drill tube is later pushed over the drill rod to drill a hole of greater diameter than that made by the drill rod 31, and concentric with this hole. If the drill rod were to be removed before the device is removed, and the drill rod is subsequently to be reinserted in the holes in the tibia and femur, this may be difficult since the crosssectiors of the holes are small and the angle between the two bones might have been changed, so that the holes are no longer in mutual alignment.

With the femur A and the tibia B in the angled position illustrated in FIG. 1 a drill shank 12 (FIG. 5) having an external screw thread on one end 12a thereof is introduced through the hole B'', or through a wider hole concentric therewith, so that the end 12a of the drill shank projects into the space between the tibia and the femur. A milling bit 13 is then screwed firmly onto the end 12a of the drill shank so that inclined milling edges 13a on the bit 13 face towards the hole B'', whereafter the drill shank 12 is rotated and the milling edges 13a pressed against the outer edge of the hole B'', to chamfer said edge to the extent desired Subsequent to unscrewing the milling bit from the shank and withdrawing the shank from the hole B'', the shank 12 is reversed and is reintroduced into the hole B'' so that the other end 12b of the shank having an internal screw thread formed therein enters the space between the tibia and the femur. The other end of the milling bit is then screwed into said other end 12b of the shank 12 and the shank is rotated while pressing the bit against the hole A'' so as to chamfer the outer edge of the hole with the milling edges 13a. Subsequent to removing the milling bit 13 from the shank 12, the shank is withdrawn from the hole B'' and the milling bit replaced on the shank in the last mentioned position, whereupon the outer edges of the holes A'' and B'' remote from the knee joint can also be chamfered by rotating the shank and urging the milling edges 13a against said hole edges.

Figure 6:
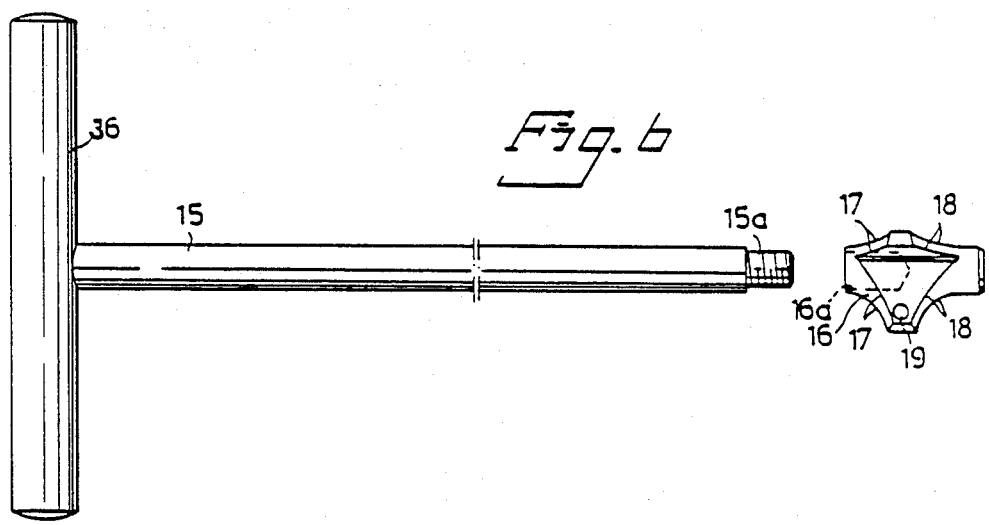
FIG. 6 is a side view of a second embodiment of a milling device for the same purpose.

A modification of the device in FIG. 5 is shown in FIG. 6, and includes a shank 15 provided with a handgrip 36. The free end of the shank 15 has an outer thread 15a. A milling bit 16 having an inner thread 16a is intended to be detachably connected to the shank 15 by means of threads 15a and 16a. The bit 16 has three pairs of curved cutting edges facing the left end of the bit and three pairs facing the right end of the bit. Some of these edges are shown in FIG. 6 and are designated 17 (the left edges) and 18 (the right edges), respectively.

The device shown in FIG. 6 is used in a manner similar to that shown in FIG. 5 to mill-off bone material from the tibia and femur B and A around the edges of the holes B" and A" drilled by the drill rod 11 or 31, and possibly widened thereafter by a drill tube described above. If the edge material of holes A" and B" is to be milled off, the shank 15 is inserted in hole B" so that its thread 15a will be placed in the space between the tibia and the femur. By using an arterial clamp for gripping the bit 16 via a hole 19 therein the bit is then inserted in said space and connected to the shank 15. Thereafter, the handgrip 36 is manually rotated in the same direction as used when connecting the threads 15a and 16a to each other, while at the same time it is pressed towards hole A" and then pulled towards hole B', or vice versa, to chamber their edges by means of edges 18 and 17, respectively. Thereafter, the arterial clamp is inserted in the space between the tibia and the femur to grip the bit 16 during rotation of the handgrip 36 in the opposite direction, thus detaching the shank 15 from the bit 16. With the shank pulled out from the hole B" the bit 16 may be attached to shank 15 again, and be used to chamfer the edges of the holes A" and B" on the outside of the bones A and B.

The chamfering of the edges of the holes A" and B" can be effected to ensure that the cruciate ligament substitute to be implanted in the knee is not subjected to wear at its outer edges during bending of the tibia relative to the femur.

A negligibly stretchable cruciate ligament substitue made of some suitable material is then inserted into the holes A" and B" and straightened, whereafter the respective ends of the ligament substitute are attached in a known manner to the tibia and the femur in the proximity of the locations of the mouths of said holes on the outer surfaces of the bones.

Some embodiments of the present invention have been described in the aforegoing with reference to the accompanying drawings. It will be understood, however, that these embodiments can be modified and that other embodiments are conceivable without departing from the concept of the invention. For example, one or more level indicators may be mounted on the device to facilitate alignment thereof (one such level indicator is shown in FIG. 1 and referenced 14). The device may have a different form with the position of alignment and the length of the tube 5 or portion 26 adapted to an angle between the tibia and the femur which is other than 90°. The device can also be implemented so that the tube 5 and the arm 3 retain their illustrated form and positions of alignment while other parts of the device are modified, for instance so that the handle and handgrip project upwardly and thereafter to the right in FIG. 1 above the femur and carry an arm corresponding to the arm 4 with the tubes 7 and 9 located in register with the tube 5 and with the edge 10 of the tube lockable against the outside of the femur, the hole A" being drilled from outside the femur immediately prior to, although in the same working stage as drilling the hole B'.

Consequently the invention is solely restricted by the statements made in the claims

We claim:

1. A device for aligning and guiding a reciprocatingly movable drill for drilling a hole through at least either the tibia or the femur forming a knee joint, in which hole one end of an anterior cruciate ligament substitute is intended to be inserted and thereafter attached to the bone, the device including a first aligning and guiding element (5; 26) intended for insertion into the space between the condyles (A') of the femur, and a second aligning and guiding element (9; 24), means for connecting the first and second aligning and guiding elements with the second element in line with the first element and adapted to be located externally of said space and spaced from the first element at a distance for bridging a part of the tibia or the femur (B, A) located adjacent the space, characterized in that the ends of the first element (5, 26) are spaced apart at a distance corresponding to the length of the cruciate ligament so as to abut both the femur and tibia (A, B) respectively at the two ligament attachment points thereof, the first aligning and guiding element having a passage (27) with a circular cross section and with a slot (30) along its whole length, the width of the slot being substantially less than the diameter of the passage the slot (30) adapted for removal of the device from a drill rod of the drill.

2. A device for aligning and guiding a reciprocatingly movable drill for drilling a hole through at least either the tibia or the femur bones forming a knee joint, in which hole end of an interior cruciate ligament substitute is intended to be inserted and thereafter attached to the bone, the device including a first aligning and guiding element (5; 26) intended for insertion into the space between the condyles (A') of the femur, and a second aligning and guiding element (9; 24), means for connecting the first and second aligning and guiding elements with the second element in line with the first element and adapted to be located externally of said space and spaced from the first element at a distance for bridging a part of the tibia or the femur (B, A) located adjacent the space, characterized in that the ends of the first element (5 26) are spaced apart at a distance corresponding to the length of the cruciate ligament so as to abut both the femur and tibia (A, B) respectively at the two ligament attachment points thereof, that the device further comprises a handle (2; 21) adapted to be set parallel to the femur and that the aligning and guiding elements (5, 9; 26, 24) form an angle of approximately 28° with said handle.

* * * * *